United States Patent [19]
York

[11] Patent Number: 5,141,506
[45] Date of Patent: Aug. 25, 1992

[54] SYSTEMS AND METHODS FOR CREATING SUBSTRATE SURFACES BY PHOTOABLATION

[76] Inventor: Kenneth K. York, Apt. No. 28, 1633 Amberwood Dr., S. Pasadena, Calif. 91030

[21] Appl. No.: 678,883

[22] Filed: Mar. 27, 1991

Related U.S. Application Data

[63] Continuation of Ser. No. 790,112, Oct. 22, 1985, abandoned.

[51] Int. Cl.$^5$ .............................................. A61M 5/06
[52] U.S. Cl. .......................................... 606/5; 606/3; 606/10; 606/13; 128/395; 128/898; 219/121.6; 219/121.68; 219/121.69; 219/121.74; 219/121.85
[58] Field of Search ...................... 128/395, 397, 398; 606/2-18; 219/121.6, 121.65-121.69, 121.72—121.75, 121.85, 121.78

[56] References Cited

U.S. PATENT DOCUMENTS

| | | | |
|---|---|---|---|
| 3,467,099 | 9/1969 | Lotmar | 128/303.1 |
| 3,586,813 | 6/1977 | Cruickshank | 128/395 |
| 3,769,963 | 11/1973 | Goldman et al. | 128/395 |
| 3,865,114 | 2/1975 | Sharon | 128/303.1 |
| 3,981,705 | 9/1976 | Jaeger et al. | 219/121 LQ |
| 4,114,018 | 9/1978 | Von Allinen et al. | 219/121 LM |
| 4,135,962 | 1/1979 | Oehrle | 219/121 LQ |
| 4,215,263 | 7/1980 | Grey | 219/121 LQ |
| 4,309,998 | 1/1982 | Aron nee Rosa et al. | 128/303.1 |
| 4,350,163 | 9/1982 | Ford, Jr. et al. | 128/633 |
| 4,391,275 | 7/1983 | Fankhauser | 128/362 |
| 4,427,872 | 1/1984 | Saunders | 219/121 LJ |
| 4,429,210 | 1/1984 | Sado et al. | 219/121 LW |
| 4,456,811 | 6/1984 | Hella et al. | 219/121 LQ |
| 4,461,294 | 7/1984 | Baron | 128/303.1 |
| 4,473,735 | 9/1984 | Steffen | 219/121 LJ |
| 4,520,816 | 6/1985 | Scharchar et al. | 606/4 |
| 4,533,812 | 8/1985 | Lorenz | 219/121 LJ |
| 4,538,608 | 9/1985 | L'Esperance | 128/395 |
| 4,558,698 | 12/1985 | O'Dell | 128/395 |
| 4,563,565 | 1/1986 | Kampfer | 2129/121 LJ |
| 4,566,765 | 1/1986 | Mijanchi et al. | 350/174 |
| 4,729,372 | 3/1988 | L'Esperance, Jr. | 606/5 |

FOREIGN PATENT DOCUMENTS 0151869  8/1985  European Pat. Off. ......... 128/303.1

OTHER PUBLICATIONS

"Excimer Laser Surgery of the Cornea" Trokel et al; Amer. J. Opthal; 96: 720-715 1983.
"Laser Beam Wire Stripping Machine" Nivens Western Electric Technical Digest #56, Oct., 1974 pp. 14-20.
"Corneal Surgery" by L. Girard, C. V. Molby Company 1981; pp. 154-170.

*Primary Examiner*—David M. Shay

[57] ABSTRACT

A system for photoablating a photoablatable substrate (such as the cornea of a human eye) to create a rounded work surface includes a curved, hollow mirror for reflecting light capable of photoablating such surfaces. The curvature of the mirror determines the shape and curvature of the rounded work surface created. The mirror has an opening of sufficient size and shape to expose the substrate to reflected, photoablating light, and is linked to a mechanism for adjusting mirror tilt and height with respect to the substrate. The system can include a source of photoablating light such as an excimer laser, a mechanism for aligning light from the excimer laser with the mirror surface, a mirror cover for excluding unreflected excimer laser light from desired portions of the substrate, and a high-speed shutter system for controlling the amount and the timing of light transmission from the excimer laser to the reflecting means.

44 Claims, 8 Drawing Sheets

SYSTEMS AND METHODS FOR CREATING SUBSTRATE SURFACES BY PHOTOABLATION

This application is a continuation of application Ser. No. 06/790,112 filed Oct. 22, 1985 now abandoned, by Kenneth K. York entitled "SYSTEMS AND METHODS FOR CREATING SUBSTRATE SURFACES BY PHOTOABLATION".

This invention relates to systems and methods for photoablating, photoablatable material to create smooth, rounded work surfaces, and, in particular, for photoablating such photoablatable material as the cornea of a human eye. The systems comprise means for reflecting photoablating light, such that reflected rays will be tangent to the surface of the proposed rounded work surface. This reflecting means has an opening of sufficient size and shape to expose some or all of the photoablatable material (substrate) to reflected light capable of photoablating and producing said rounded work surfaces. Preferably, the reflecting means is linked to means for adjusting its height and tilt with respect to the photoablatable substrate, and to other means for fixing and adjusting, as desired, the angle of incidence of photoablating light on the surface of the reflecting means. In turn, such adjusting means determine the angle at which photoablating light is reflected, and works upon the substrate to produce the required rounded work surface. The adjusting means also controls the amount and location of the substrate that is photoablated. Preferably, these systems also include means for determining, adjusting and fixing the path of photoablating light from its source to the surface of the reflecting means. As a result, the photoablating light is preferably kept substantially coaxial with the axis of revolution of the reflecting means.

In use, the reflecting means is linked to means for generating light capable of photoablating the substrate. Preferably, this photoablating light comprises intense, coherent, ultrashort pulsed, collimated ultraviolet light (UV) (such as light produced by an excimer laser having a wavelength in the range of about 150 to about 250 nanometers). Ultrashort pulses of longer wavelengths may have similar effects. Preferably, the fluence (i.e., the power density) of the photoablating light is in the range of about 20 to about 1,000 millijoules per square centimeter per pulse for a wavelength of 193 nm.

Preferred embodiments of these systems may also include a cover means for the reflecting means to admit photoablating light only to the surface of the reflecting means, and to exclude unreflected photoablating light from direct contact with all or a part of the substrate. Where the source of photoablating light is an excimer laser or other source of high-intensity UV light, this cover means is preferably a shield having portions substantially transparent to, and portions substantially opaque to the photoablating wavelength of light.

These systems can also, in preferred embodiments, include a shutter system, preferably an ultrahigh speed shutter system, for the source of photoablating light. Preferably, such a shutter system has a speed on the order of nanoseconds. The shutter system is preferably under control of means for opening and closing the shutter in response to a signal indicating that the reflecting means is properly aligned with the source of photoablating light.

These systems can also include means for aiming and aligning the source of photoablating light with the reflecting means. In preferred embodiments, another light source, coaxial with the source of photoablating light, and a means for detecting its reflection, can be used to detect the angle of incidence of this light on the reflecting means and thereby align the light from the photoablating light source with the reflecting means. In preferred embodiments, this means for aiming and aligning the source of photoablating light is a coaxial aiming laser such as a helium neon laser or other laser capable of emitting non-photoablating light coaxial with light from the photoablating light source. A photodetector or other means for detecting the proper alignment of the light from the aiming means can be used to detect whether the light from the photoablating source is properly aimed at, and focused upon the reflecting means. In turn, the signal from the means for detecting proper alignment of light from the aiming means with the reflecting means can be used to control the means for opening and closing the shutter in the shutter system to deliver photoablating light of proper intensity, at the proper time, and for the proper duration to the reflecting means, and from there, to the substrate.

The reflecting means itself is curved, preferably aspheric, and can have a smooth, curved surface or a Fresnel surface.

This invention also provides methods for photoablating substrates comprising placing means for reflecting light capable of photoablating said substrate over said substrate; directing light capable of photoablating said substrate onto a reflecting means of sufficient curvature at an angle of incidence sufficient to direct reflected, photoablating light across, and to photoablate material from the substrate; and adjusting the angle of incidence between the photoablating light and said reflecting means in a degree sufficient to remove from said substrate a predetermined quantity of material in a predetermined pattern and shape. Where the substrate is the cornea, the predetermined quantity, pattern and shape of the material removed can correct refractive errors such as myopia, hyperopia and astigmatism, eliminating the need for eyeglasses and contact lenses. This cornea-shaping process is sometimes called photokeratomileusis.

This invention can better be understood by reference to the accompanying drawings in which.

Figure 1:
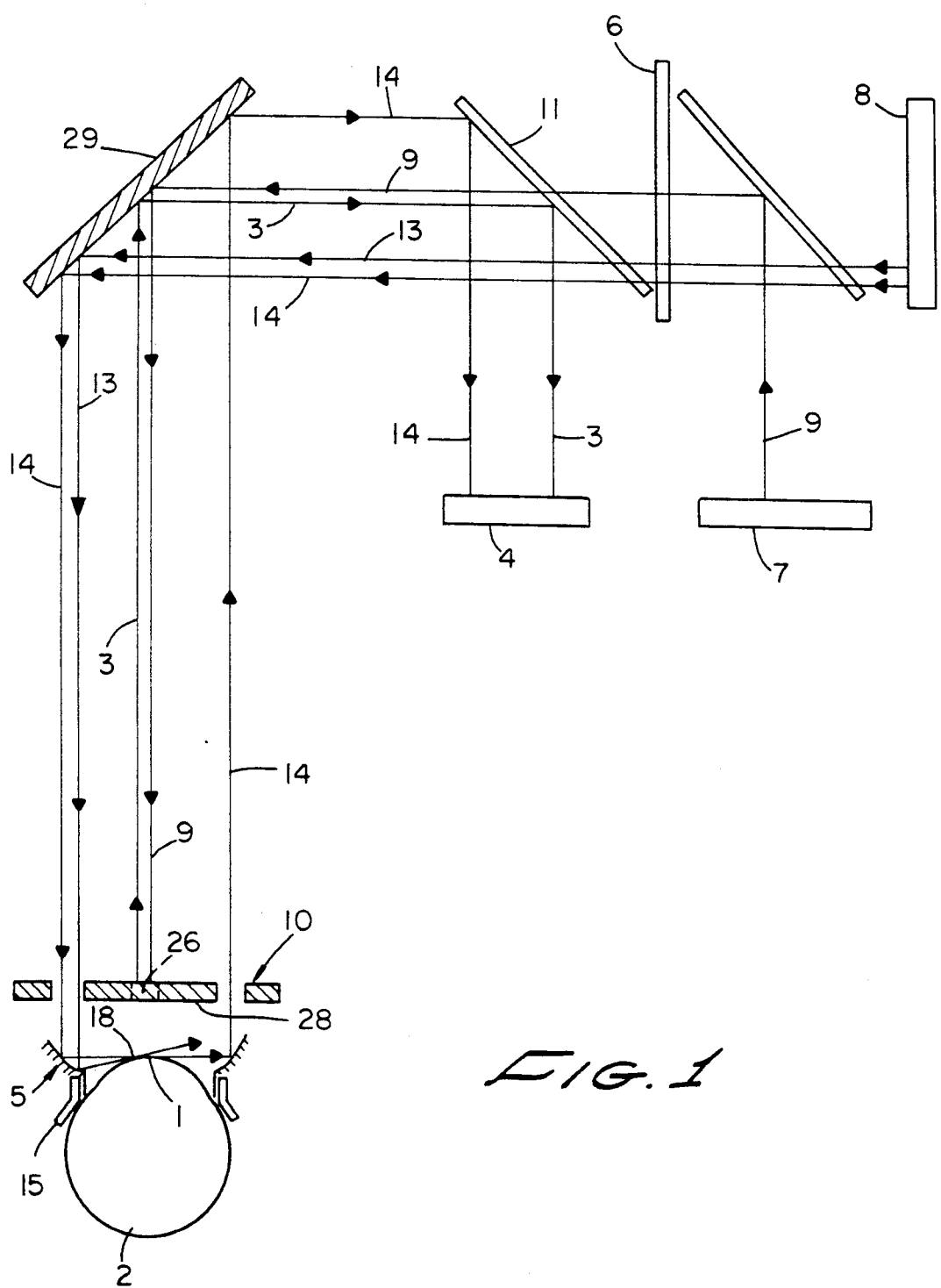
FIG. 1 is a schematic diagram of a preferred embodiment of the new photoablating system, here used to photoablate tissue from the cornea of a human eye.
Figure 6:
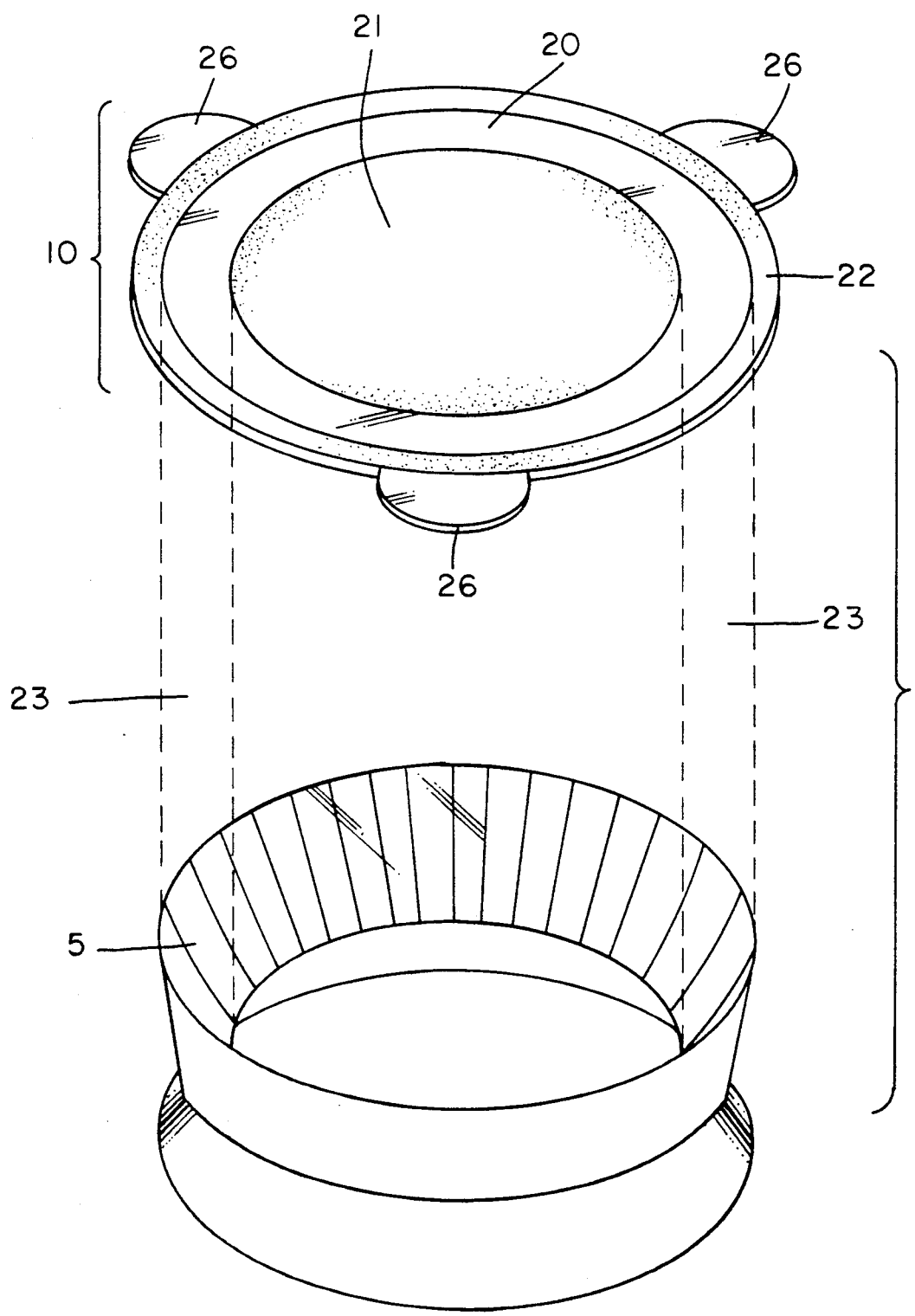

FIG. 6 is an exploded view of the preferred embodiment of the mask for use with the embodiment illustrated in FIG. 1. This figure shows the ring-shaped UV transparent window that corresponds to the dimensions of the reflecting means when viewed along the axis of revolution of the reflecting means. This figure also shows the mirrors extending from the mask. The mirrors may be used for aligning the laser and the reflecting means.

Figure 7:
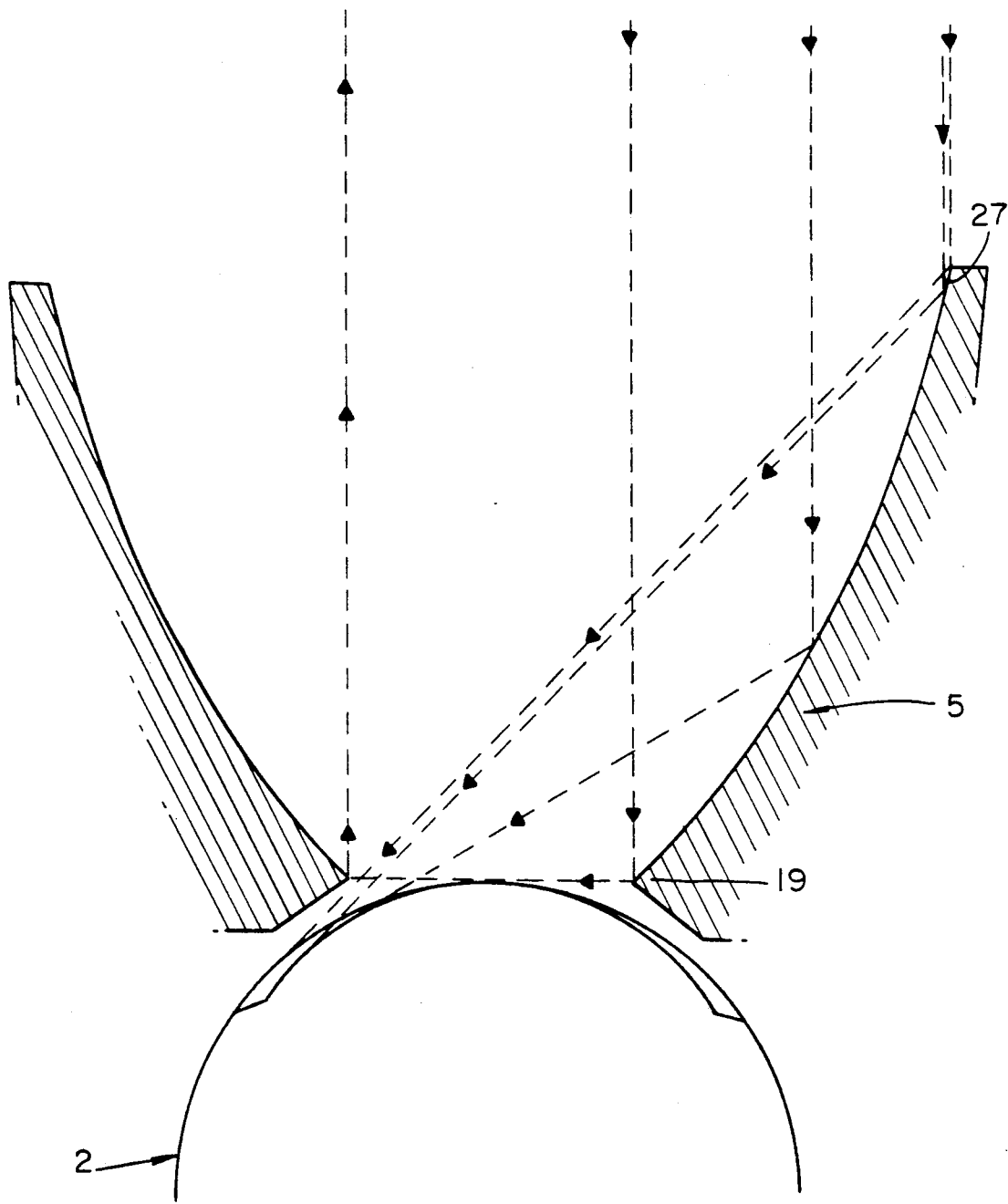
Figure 8:
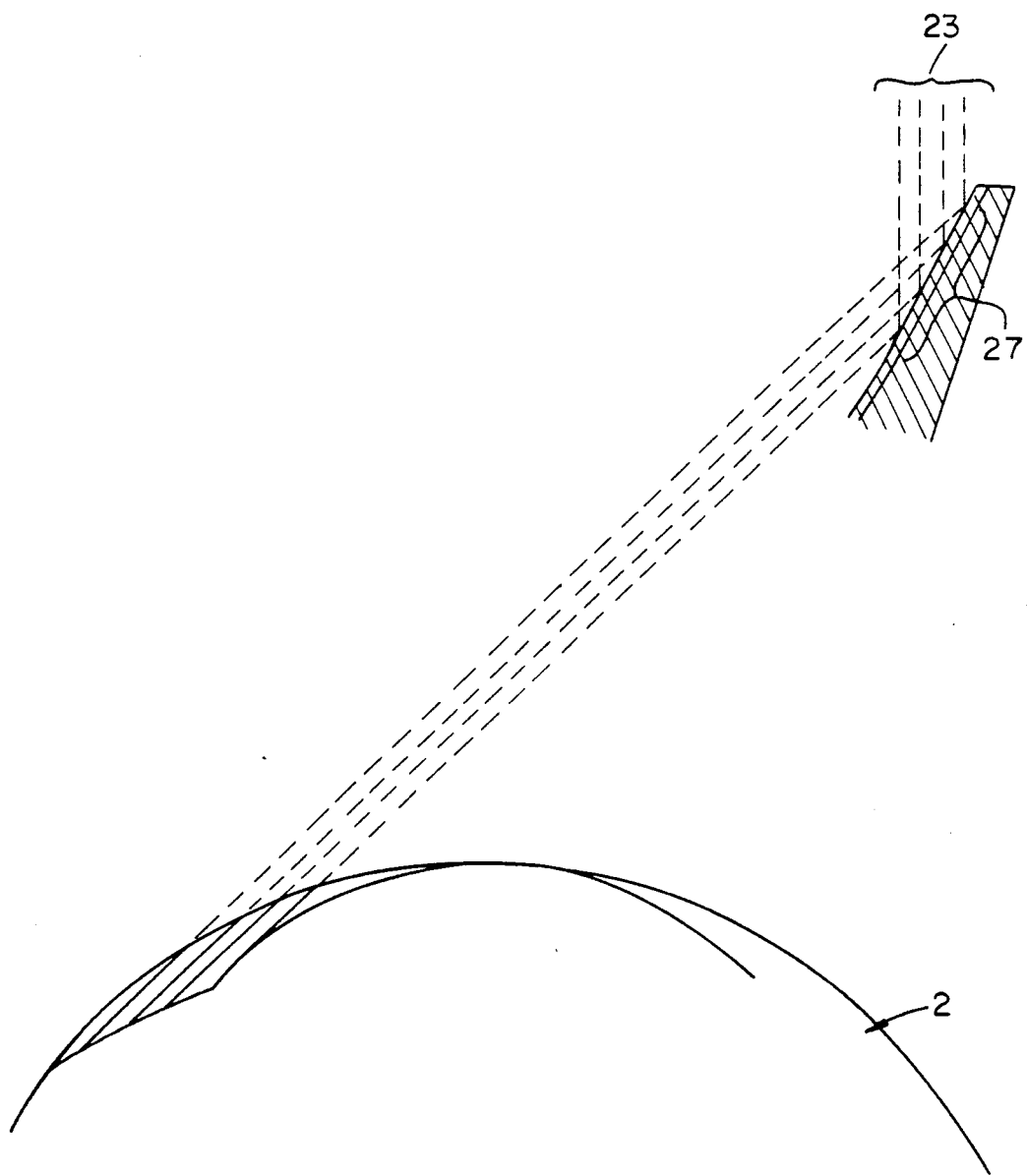

FIGS. 7 and 8 are additional illustrations showing the effects of plano portions at the top or bottom of the reflecting means in the new photoablating systems, and in particular in the preferred embodiment shown in FIG. 1.

Figure 2:
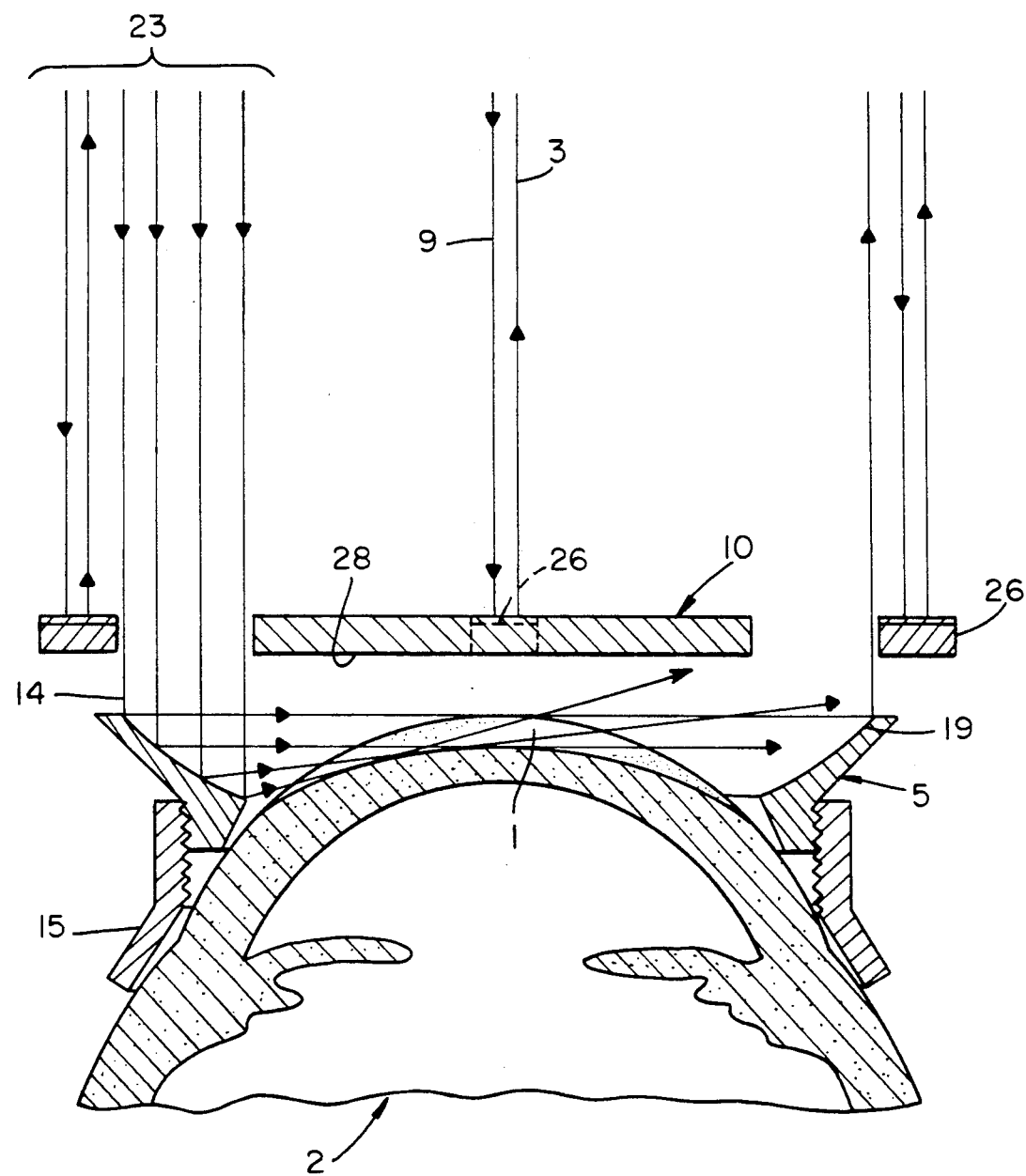
FIG. 2 is an exploded, fragmentary view of a part of the system shown in FIG. 1.
Figure 3:
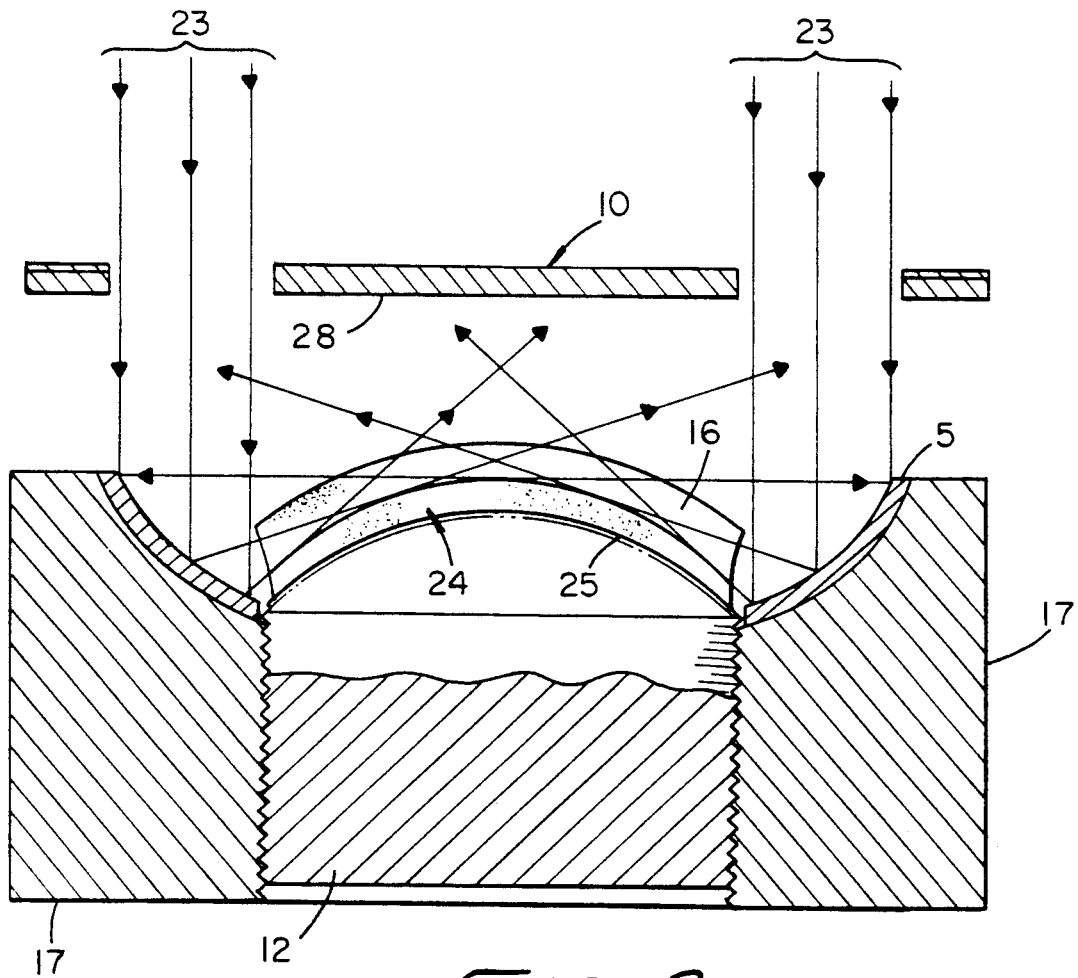
FIG. 3 is an exploded view of the system shown in FIG. 1, here used to shape corneal tissue into a lenticule ex situ by photoablation.
Figure 9:
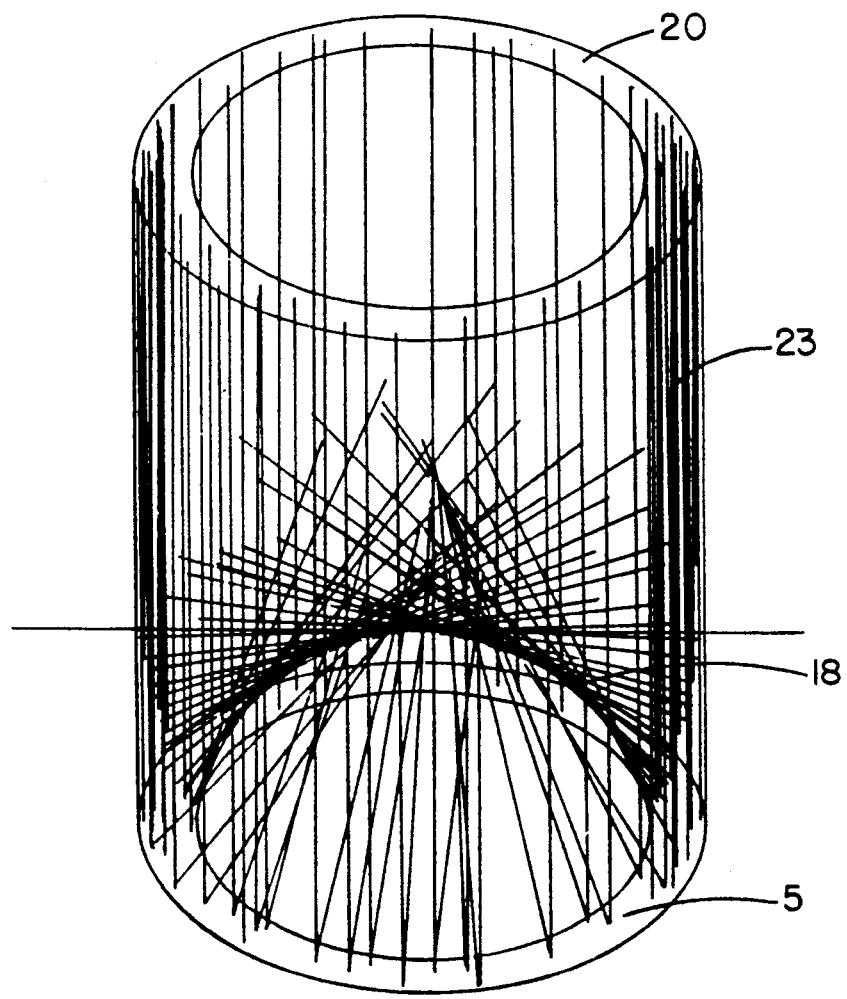

FIG. 9 shows the hollow cylinder of photoablating light produced by the mask in the preferred embodiment of the new system shown in FIGS. 1-3.

FIGS. 1 and 2 show a preferred embodiment of a system for photoablating tissue from cornea 1 of a human eye 2. Reflecting means, here curved, ring-shaped mirror 5, reflects coherent, collimated, intense UV light from excimer laser 8 across corneal surface 1. Mirror 5 has a far UV reflective coating such as an enhanced aluminum or multi-layered dielectric coating. The curved shape of mirror 5 causes a hollow cylinder of UV light to be reflected over corneal surface 1 in the shape of a hollow dome of light. This dome can have any desired radius of curvature, and can be spherical or aspherical in shape.

Each ray of UV light reflected from the curved mirror surface 5 is tangent to some point on the surface of the dome. Corneal tissue struck by the dome of reflected UV light is volatilized, leaving the remaining cornea with a new curvature corresponding to the inner surface of the dome. The corneal surface curvature obtained can be precisely and accurately predetermined by modifying the shape and curvature of the mirror 5 which determines the shape and radius of curvature of the dome of UV light. Since substantially all of the UV light that touches the cornea is reflected and tangent to the new corneal surface, and since far UV light at 193 mm is absorbed in the first few microns of corneal tissue, the amount of far UV light reaching the lens and retina of eye 12 is minimal.

Figure 4:
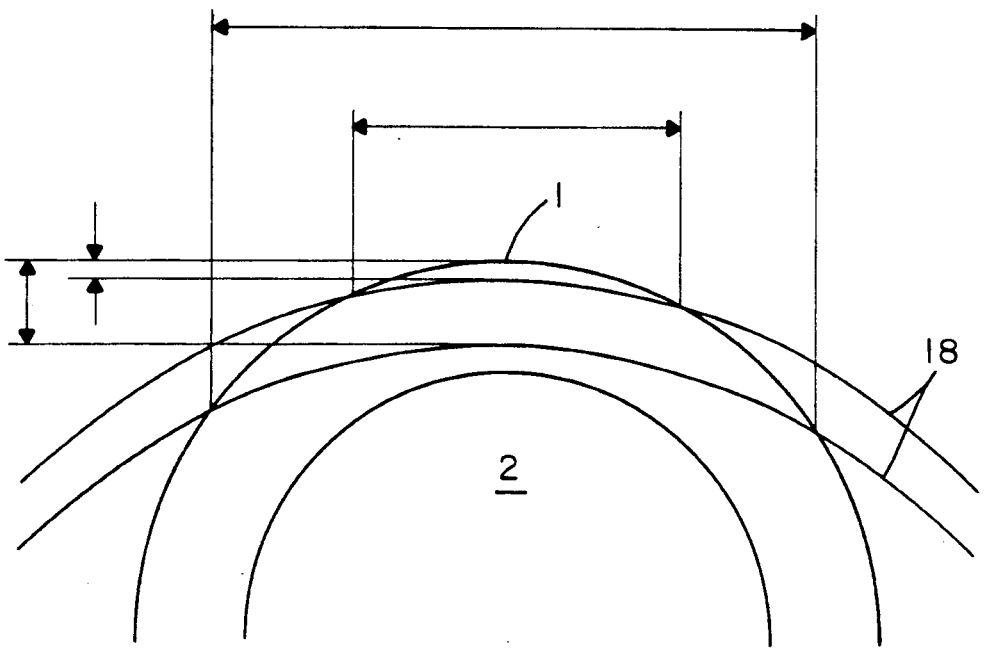
FIG. 4 is a schematic diagram illustrating how the adjustment in height of the reflecting means affects the amount of corneal tissue that is photoablated and hence the size of the optical zone created by the embodiment illustrated in FIG. 1.

Holder 15 positions mirror 5 on eye 2, and provides means for adjusting the height of mirror 5 relative to the apex of the corneal surface 1. The height of mirror 5 relative to the corneal apex determines the amount of corneal tissue that is photoablated, and hence the size of the optical zone created, i.e., the central cornea used for image formation. An optical zone that is too small causes glare and distortion. The size of the optical zone may be increased by decreasing the height of the mirror relative to the corneal apex, but only at the expense of further thinning of the cornea, as FIG. 4 shows. A screw-type mechanism or piezo-electric crystal translator can provide the means for the height adjustment. Optical zone size and the maximum possible change in refractive power of the cornea through this system are inversely proportional. Tilt is controlled by repositioning holder 15 and mirror 5 on the eye. The alignment laser 7 confirms proper tilt adjustment.

Light from aiming laser 7, coaxial with light from excimer laser 8, strikes three small plano mirrors 26 on mask 10 or the 45° angulated portion 19 of mirror 5 shown in FIGS. 1, 5A, 5B, 5C and 7, and is reflected to photodetector 4 via beam splitter 11 only when mirror 5 is accurately and precisely aligned. For example, in FIG. 1, light beam 9 from coaxial laser 7 is reflected in this way to photodetector 4 as light beam 3.

Figure 5A:
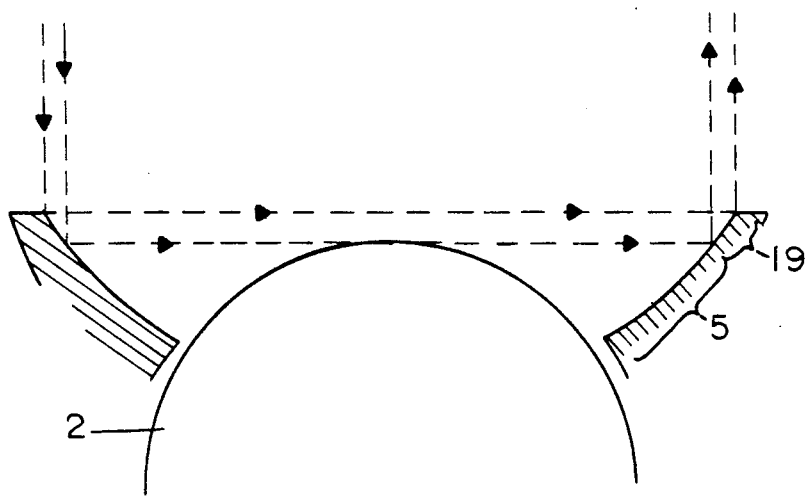
FIGS. 5A, 5B and 5C show the effects of including plano portions in the reflecting means of the embodiment illustrated in FIG. 1. The reflected light from these 45° angulated plano mirrors can be used to determine the height of the reflecting means relative to the apex.
Figure 5B:
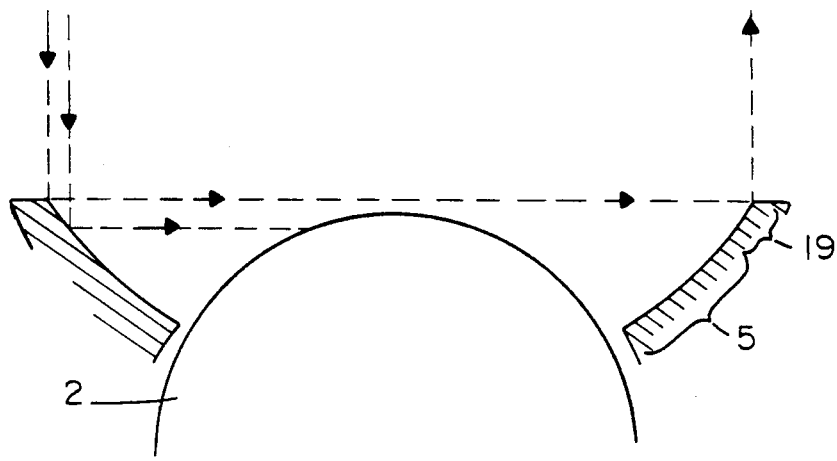
Figure 5C:
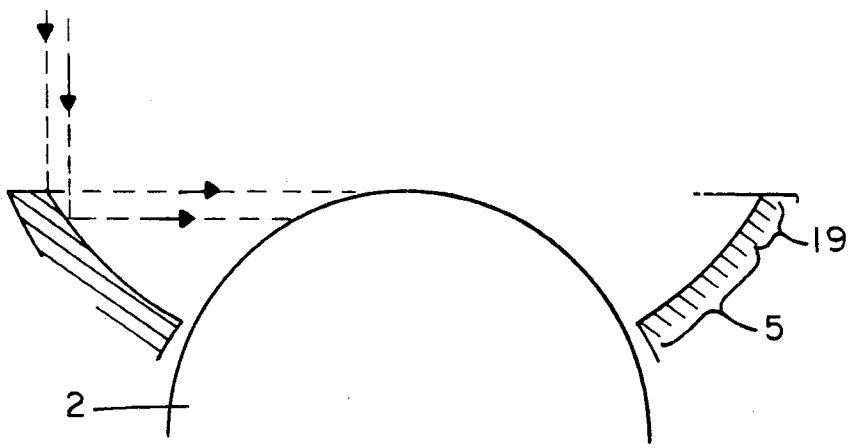

As FIGS. 5A, 5B and 5C show, if plano portions 19 of the mirror 5 are at the bottom and oriented at 45° angles to the laser source, laser light is reflected back to a photodetector on the laser. The position of the reflecting means relative to a substrate in its aperture determines whether the laser light is reflected or blocked. This phenomenon can be used to determine the position of the mirror relative to the substrate, and thereby determine the amount of substrate to be photoablated.

As seen in FIG. 6, mask 10, preferably made of a combination of UV transparent material such as quartz or fused silica, and UV opaque (but visible light transparent) glass such as a UV filter, permits only a hollow cylinder of UV light 33 to pass through UV transparent zone 20 to reach mirror 5 (see FIG. 9). The inside and outside diameters of this hollow cylinder of UV light 23 from the excimer laser correspond to the dimensions of aspheric mirror 5 when viewed from above. When the axes of mirror 5 and the cylinder of UV light from excimer laser 8 are properly aligned, mirror surface 5 is fully and evenly illuminated. Zones 21 and 22 of mask 10 prevent UV light from directly striking the cornea, lens, retina and other ocular structures in the human eye, and provide a target to focus on for purpose of aligning axes of eye 2, mirror 5 and light from laser 8.

In operation, if photodetector 4 senses reflected light beam 3 from aiming laser 7, then the light from excimer laser 8 will precisely and accurately fall on mirror 5. When photodetector 4 receives a signal to this effect, ultrafast shutter 6, which can be an electro-optic shutter opens, permitting light beams 13 and 14 from excimer laser 8 to pass to curved mirror 5. From there, the excimer light passes to corneal surface 1 as reflected, dome-shaped UV photoablating light. A microprocessor can be used to control shutter 6 precisely and accurately. UV plano mirror 29 allows horizontal laser beam to be projected onto the eye of a patient in the supine position.

As FIGS. 7 and 8 show, curved reflecting means 5 can have plano portions at top 27 or bottom 19. The plano mirrors at the top reflect parallel rays onto the substrate and may be employed to remove substrate in a particular fashion (i.e., to create a smooth transition area outside the optical zone). This effect is energy dependent, unlike the creation of curved surfaces that do not change shape if overtreated.

FIG. 3 shows the application of the system illustrated in FIGS. 1 and 2 to the photoablation of corneal button 16 to produce lenticule 24. Here, the hollow cylinder of excimer laser light 23 passes through mask 10, and is reflected from ring-shaped, aspheric mirror 5 across corneal button 16. Again, the reflected UV light is a hollow dome 18 of any desired radius of curvature, and can be spherical or aspherical. Corneal button 16 is held firmly over the convex-shaped surface 25 of cylindrical lenticule holder 12 by vacuum or other means. Threaded height adjustor 17 permits adjustment of the height of mirror 5, and that controls the amount of corneal tissue to be photoablated in forming corneal lenticule 24, thereby determining lenticule thickness and the optical zone size. The undersurface of mask 10 (FIGS. 1-3) has absorbent antireflective UV coating 28 to prevent undesirable light scattering.

What is claimed is:

1. A system for removing material from a substrate comprising means for reflecting light into the form of a hollow dome of any desired shape onto said substrate such that there is a reflected light ray tangential to substantially every point on the surface of the proposed, desired shape, and such that there are substantially no light rays striking the substrate below the surface of the proposed, desired shape, said light being capable of removing material from said substrate, said reflecting means having a size and shape sufficient to expose said substrate to reflected light and to form a surface of said proposed, desired shape on said substrate; means for generating light capable of removing material from said substrate; and means for adjusting the angle of incidence of light on said reflecting means and, in turn, adjusting the pattern of irradiation of said substrate.

2. A system for photoablating material from a substrate comprising means for reflecting light capable of photoablating material from said substrate, said reflecting means having a size and shape sufficient to expose said substrate to reflected, photoablating light rays and to form a surface of predetermined shape on said substrate; means for generating said photoablating light; and means for adjusting the angle of incidence of said photoablating light rays on said reflecting means to photoablate said substrate into a predetermined, desired shape so that said light rays are substantially tangential to said surface in said predetermined desired shape.

3. A system for photoablating material from a substrate comprising means for reflecting light capable of photoablating material to photoablate material from said substrate, said reflecting means having a size and shape sufficient to expose said substrate to reflected, photoablating light to produce a surface of predetermined desired shape, said reflecting means being a ring-shaped, curved mirror with a central aperture; means for generating light capable of photoablating said photoablatable material; and means for adjusting the angle of incidence of said photoablating light on said reflecting means, and in turn, on said substrate.

4. The system of claim 3 further comprising means adapted for holding a cornea of a human eye as said substrate.

5. The system of claim 3 wherein said means for generating light capable of photoablating said substrate comprises an excimer laser.

6. The system of claim 3 wherein said means for generating light capable of photoablating said substrate is a source of coherent, intense, collimated light having a wavelength in the range of 150 to 250 nanometers and a power density in the range of 20 to 1000 millijoules per square centimeter per pulse.

7. The system of claim 3 wherein said reflecting means can be adjusted in height relative to said substrate further comprising means for controlling the amount of material to be photoablated from said substrate including means for adjusting the height of the reflecting means relative to the photoablatable material.

8. The system of claim 3 wherein said reflecting means can be tilted relative to said substrate, relative to said photoablating light, or both, further comprising means for adjusting the angle of incidence of said photoablating light on said reflecting means, and adjusting the pattern of irradiation of the substrate including means for adjusting said tilt.

9. The system of claim 3 further comprising means for excluding a portion of the photoablating light from directly striking the substrate, and for confining said photoablating light to incidence upon said reflecting means.

10. The system of claim 3 further comprising means for aiming and aligning the means for generating photoablating light with said reflecting means.

11. The system of claim 3 further comprising means for determining whether said reflecting means is properly aligned with the angle of incidence of light from said means for generating photoablating light, and shutter means for permitting or preventing light from said means for generating photoablating light to pass to said reflecting means in response to detection of proper alignment.

12. A system for photoablating material from a substrate comprising means for reflecting light capable of photoablating material to photoablate material from said substrate, said reflecting means having a shape and size sufficient to expose said substrate to reflected, photoablating light rays to produce a projecting surface of predetermined, curved shape with said light rays substantially tangential to said surface of said predetermined curved shape; means for generating light capable of photoablating said photoablatable material; and means for adjusting the angle of incidence of said photoablating light rays on said reflecting means and, in turn, on said substrate.

13. The system of claim 12 further comprising means adapted for holding a cornea of a human eye as said substrate.

14. The system of claim 12 wherein said reflecting means is a ring-shaped, curved mirror with a central aperture.

15. The system of claim 12 wherein said means for generating light capable of photoablating said substrate comprises an excimer laser.

16. The system of claim 12 wherein said means for generating light capable of photoablating said substrate comprises a source of coherent, intense, collimated light having a wavelength in the range of 150 to 250 nanometers and a power density in the range of 20 to 1000 millijoules per square centimeter per pulse.

17. The system of claim 12 wherein said reflecting means can be adjusted in height relative to said substrate further comprising means for controlling the amount of material to be photoablated from said substrate including means for adjusting the height of the reflecting means relative to the photoablatable material.

18. The system of claim 12 wherein said reflecting means can be tilted relative to said substrate, relative to said photoablating light, or both, further comprising means for adjusting the angle of incidence of said photoablating light on said reflecting means, and adjusting the pattern of irradiation of the substrate including means for adjusting said tilt.

19. The system of claim 12 further comprising means for excluding a portion of the photoablating light from directly striking the substrate, and for confining said photoablating light to incidence upon said reflecting means.

20. The system of claim 12 further comprising means for aiming and aligning the means for generating photoablating light with said reflecting means.

21. The system of claim 12 further comprising means for determining whether said reflecting means is aligned as desired with the angle of incidence of light from said means for generating photoablating light, and shutter means for permitting or preventing light from said means for generating photoablating light to pass to said reflecting means in response to detection of proper alignment.

22. The system of claim 12 wherein said reflecting means includes an opening, and further comprising means for holding a button of corneal tissue near said opening so that reflected photoablating light produces a corneal lenticule of desired curvature and dimensions.

23. The system of claim 12 wherein said reflecting means includes an opening, and further comprising means for holding said substrate near said opening in said reflecting means in order that reflected photoablating light may produce the desired rounded work surface.

24. The system of claim 18 wherein said substrate is a donor corneal button having a convex anterior and a concave posterior surface and said holding means has a convex end complementing said concavity of said posterior donor surface or an end complementary to the convex anterior of a cornea of the proposed recipient.

25. A system for photoablating material from a substrate comprising means for reflecting light capable of photoablating material to photoablate material from said substrate, said reflecting means having a size and shape sufficient to expose said substrate to reflected, photoablating light to produce surface of predetermined, desired shape, said reflecting means including an opening; means for holding said substrate near said opening so that reflected photoablating light may produce said predetermined, desired shape on said surface; means for generating light capable of photoablating said photoablatable material; and means for adjusting the angle of incidence of said photoablating light on said reflecting means and, in turn, on said substrate.

26. The system of claim 25 wherein said holding means comprises means adapted for holding a button of corneal tissue near said opening so that reflected photoablating light produces a corneal lenticule of desired curvature and dimensions.

27. The system of claim 26 wherein said substrate is a donor corneal button having a convex anterior and a concave posterior surface and said holding means has a convex end complementing said concavity of said posterior donor surface or an end complementary to the convex anterior of a cornea of the proposed recipient.

28. A system for removing material from a substrate comprising means for reflecting light into the form of a hollow dome-shaped pattern of any desired shape onto said substrate, said light being capable of removing material from said substrate, said reflecting means having a size and shape sufficient to expose said substrate to reflected light and to form a surface of predetermined shape on said substrate, said reflecting means comprising a ring-shaped, curved mirror with a central aperture; means for generating light capable of removing material from said substrate; and means for adjusting the angle of incidence of light on said reflecting means and, in turn, adjusting the pattern of irradiation of said substrate.

29. The system of claim 28 further comprising means for holding, as said substrate, the cornea of a human eye.

30. The system of claim 28 wherein the quantity of material removed from said substrate is, in part, a function of the height of said reflecting means and therefore said reflected hollow dome of light relative to said substrate, said system further comprising means for adjusting said height.

31. The system of claim 28 wherein said desired angle of incidence is, in part, a function of the tilt of said reflecting means relative to said substrate further comprising means for adjusting said tilt.

32. The system of claim 28 further comprising means for excluding a portion of the shaping light from directly striking the substrate, and for confining the shaping light to incidence upon said reflecting means.

33. A system for removing material from a substrate comprising means for reflecting light into the form of a hollow dome-shaped pattern of any desired shape onto said substrate, said light being capable of removing material from said substrate, said reflecting means having a shape and size sufficient to expose said substrate to reflected, light rays and to form a surface of predetermined shape on said substrate with said light ray substantially tangential to said surface of predetermined shape; means for generating light capable of removing material from said substrate; and means for adjusting the angle of incidence of light on said reflecting means and, in turn, adjusting the pattern of irradiation of said substrate.

34. The system of claim 33 further comprising means for holding, as said substrate, the cornea of a human eye.

35. The system of claim 33 wherein said reflecting means is a ring-shaped, curved mirror with a central aperture.

36. The system of claim 33 wherein the quantity of material removed from said substrate is, in part, a function of the height of said reflecting means and therefore said reflected hollow dome of light relative to said substrate, said system further comprising means for adjusting said height.

37. The system of claim 33 wherein said desired angle of incidence is, in part, a function of the tilt of said reflecting means relative to said substrate further comprising means for adjusting said tilt.

38. The system of claim 33 further comprising means for excluding a portion of said light from directly striking the substrate, and for confining said light to incidence upon said reflecting means.

39. A method for removing material from a substrate comprising directing light onto a reflecting means at a desired, predetermined angle of incidence sufficient to direct reflected light tangentially on said substrate in the form of a hollow dome of any desired shape or pattern to remove a predetermined, desired quantity of material from said substrate; and selecting the curvature of said reflecting means and adjusting said angle of incidence in a degree sufficient to remove material from said substrate in conformity with a predetermined pattern.

40. A method for photoablating a photoablatable substrate comprising directing light capable of photoablating such a substrate onto reflecting means of a predetermined, desired curvature at an angle of incidence adjusted sufficiently to direct reflected, light rays on, and to photoablate material from said substrate; and selecting said desired curvature of said reflecting means and adjusting the angle of incidence between the photoablating light and said reflecting means in a degree sufficient to remove from said photoablatable material a predetermined quantity of material in a predetermined pattern and shape to produce a projecting surface of predetermined, curved shape with said light rays substantially tangential to said surface of predetermined, curved shape.

41. The method of claim 40 further comprising placing means including an aperture for reflecting light capable of photoablating a rounded work surface over such a substrate with said substrate in an appropriate position relative to said aperture in the reflecting means such that reflected photoablating light produces the desired rounded work surface.

42. The method of claim 41 wherein said photoablatable material is the cornea of a human eye, and further comprising an excimer laser as the means for producing the light capable of photoablating the substrate.

43. A method for photoablating a photoablatable substrate comprising directing light capable of photoablating such a substrate onto reflecting means of a predetermined, desired curvature at an angle of incidence adjusted sufficiently to direct reflected, photoablating light at, and to photoablatable material from, said substrate, said reflecting means including an aperture placing said reflecting means over said substrate in an appropriate position relative to said aperture so that reflected photoablating light produces a predetermined, rounded shape on the surface of said substrate; and selecting said desired curvature of said reflecting means and adjusting the angle of incidence between the photoablating light, and said reflecting means in a degree sufficient to remove from said photoablatable material a predetermined quantity of material in a predetermined pattern and shape to produce said predetermined, rounded shape.

44. The method of claim 43 wherein said photoablatable material is the cornea of a human eye, and further comprising an excimer laser as the means for producing light capable of photoablating the substrate.

* * * * *